(12) United States Patent
Wenk et al.

(10) Patent No.: US 8,653,289 B2
(45) Date of Patent: Feb. 18, 2014

(54) PARTIAL ESTERS OF A POLYGLYCEROL WITH AT LEAST ONE CARBOXYLIC ACID AND ONE POLYFUNCTIONAL CARBOXYLIC ACID, THEIR PREPARATION AND USE

(75) Inventors: Hans Henning Wenk, Mülheim an der Ruhr (DE); Juergen Meyer, Essen (DE); Stefan Bergfried, Essen (DE); Hannelore Foetsch, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 358 days.

(21) Appl. No.: 13/038,774

(22) Filed: Mar. 2, 2011

(65) Prior Publication Data

US 2011/0300082 A1 Dec. 8, 2011

(30) Foreign Application Priority Data

Mar. 5, 2010 (DE) .......................... 10 2010 002 609

(51) Int. Cl.
*A23D 9/00* (2006.01)
*C11C 3/00* (2006.01)
*A01N 37/00* (2006.01)
*A61K 8/00* (2006.01)

(52) U.S. Cl.
USPC ............ 554/227; 554/166; 424/59; 424/70.9; 514/547

(58) Field of Classification Search
USPC ............ 554/166, 227; 424/59, 70.9; 514/547
See application file for complete search history.

(56) References Cited

U.S. PATENT DOCUMENTS

| | | | |
|---|---|---|---|
| 5,147,644 A | 9/1992 | Oppenlaender et al. | |
| 5,736,581 A | 4/1998 | Ansmann et al. | |
| 6,242,499 B1 * | 6/2001 | Gruning et al. | ............... 514/785 |

FOREIGN PATENT DOCUMENTS

| | | | | |
|---|---|---|---|---|
| DE | 4409569 C1 | 8/1995 | | |
| EP | 0451461 B1 | 10/1991 | | |
| EP | 0 835 862 A1 | 4/1998 | | |
| EP | 1 683 781 A2 | 7/2006 | | |
| WO | WO0172683 A1 | 10/2001 | | |
| WO | WO 2004/112731 A2 | 12/2004 | | |
| WO | WO 2006/034992 A1 | 4/2006 | | |
| WO | WO 2006034992 A1 * | 4/2006 | ............... A61K 8/06 | |
| WO | WO 2008/092676 A1 | 8/2008 | | |

OTHER PUBLICATIONS

European Search Report dated Sep. 24, 2012, received in a corresponding foreign application.
Pissavini, M. et al., "In vitro assessment of water resistance of sun care products: a reproducible and optimized in vitro test method", International Journal of Cosmetic Science, 2007, 29, pp. 451-460.

* cited by examiner

*Primary Examiner* — Deborah D Carr
(74) *Attorney, Agent, or Firm* — Scully, Scott, Murphy & Presser, P.C.

(57) ABSTRACT

The present disclosure relates to specific (poly-)glycerol partial esters with at least one carboxylic acid and one polyfunctional carboxylic acid, and to the use thereof as emulsifier and to formulations comprising partial esters of the present disclosure.

15 Claims, No Drawings

PARTIAL ESTERS OF A POLYGLYCEROL WITH AT LEAST ONE CARBOXYLIC ACID AND ONE POLYFUNCTIONAL CARBOXYLIC ACID, THEIR PREPARATION AND USE

FIELD OF THE INVENTION

The present invention relates to specific (poly-)glycerol partial esters with at least one carboxylic acid and one polyfunctional carboxylic acid, and to the use thereof as emulsifiers and formulations comprising partial esters according to the present invention.

BACKGROUND

In recent years, there has been a strong trend in the cosmetics market in the direction of the most natural products possible. In order to be able to satisfy this, it is necessary to be able to offer high-performance emulsifiers based on renewable raw materials.

Customary emulsifiers in cosmetics often contain polyethylene glycol groups (PEG) as hydrophilic groups; the compounds including PEG groups can be prepared by polymerization of ethylene oxide obtained by a petrochemical route. Since all of the raw materials used in formulations that are as natural as possible should originate from renewable sources, PEG-containing emulsifiers are undesired in such formulations.

Polyglycerol esters are a preferred PEG-free alternative to cosmetic emulsifiers based on renewable raw materials.

The use of polyglycerol esters in cosmetics as emulsifier is well-known technology. EP-B-0 835 862 describes polyglycerol partial esters which are obtainable by esterifying a polyglycerol mixture with a degree of esterification of the polyglycerol between 30 and 75% and saturated or unsaturated, linear or branched fatty acids having 12 to 22 carbon atoms and dimer fatty acids with an average functionality of from 2 to 2.4. The polyglycerol partial esters described in EP-B-0 835 862 have the advantage that in particular the freeze-stability of these emulsions is very good. However, the emulsions are still relatively viscous and are water-in-oil (W/O) emulsions, for which reason these polyglycerol partial esters are primarily suitable for producing rich lotions and creams.

A further alternative for PEG-free natural emulsifiers is also citric acid esters. The use of esters of citric acid in cosmetics, as an emulsifier or a solubilizer, has been known for a long time; thus, for example, the O1W emulsifier glyceryl stearate citrate, (2-hydroxy-1,2,3-propanetricarboxylic acid 1,2,3-propanetriol monooctadecanoate, INCI Glyceryl Stearate Citrate, CAS 39175-72-9), the citric acid ester of glyceryl stearate, is commercially available, inter alia, under the name AXOL C 62 from Evonik Goldschmidt WO2006034992 and WO2008092676 describe, for example, a cosmetic oil-in-water (O/W) emulsion comprising glyceryl stearate citrate in conjunction with further emulsifiers.

WO2004112731 describes an O/W emulsifier comprising glyceryl oleate citrate and a viscosity modifier.

A disadvantage of using citric acid esters is their high hydrolysis sensitivity, which usually limits the scope of use of these emulsifiers to a pH range from 5.5 to 8. This is particularly disadvantageous for developing cosmetic formulations that are as natural as possible which are intended, for example, to correspond to Ecocert. For cosmetic products which are to correspond to Ecocert requirements, generally only organic acids such as benzoic acid or sorbic acid can be used for preservation; these, in turn, require a pH of the emulsions of 4-5. Consequently, customary citric acid esters cannot be used in such formulations.

Simple polyglycerol esters, such as, for example, polyglycerol-3 distearate, are generally characterized by a limited formulation flexibility which is exhibited, for example, in emulsion instabilities in critical emulsion systems.

Mixed esters of polyglycerol and methylglucose and stearic acid, such as, for example, polyglyceryl-3 methylglucose distearate have an excellent stabilization potential and a broad spectrum of use. However, the methyl groups present in these products are based on the raw material methanol, and are therefore in part also of petrochemical origin.

In principle, it is also possible to use sorbitan esters or sucrose esters as O/W emulsifiers. A customary combination is, for example, sorbitan stearate and sucrose cocoate. However, these combinations are also generally characterized by a limited emulsion stabilization and low formulation flexibility.

SUMMARY

The present invention provides an emulsifier which is based completely on renewable raw materials (i.e., for example, in the synthesis, neither ethylene oxide, methanol, chlorine nor sulphur derivatives are used) and which is also suitable for formulating O/W emulsions (creams, lotions) with excellent storage stability and a pleasing care skin feel.

Surprisingly, it has been found that the (poly-)glycerol partial esters described below can be used to achieve an emulsifier that is based completely on renewable raw materials, which emulsifier exhibits excellent storage stability and is pleasing to the skin.

The present invention therefore provides (poly-)glycerol partial esters with one or more carboxylic acids having 10 to 24 carbon atoms and radicals of a polyfunctional carboxylic acid, comprising polyfunctional carboxylic acid ester (poly-) glycerol partial ester of the general formula (I) as described herein below, a process for their preparation, their use as emulsifier and formulations which comprise the same.

Advantages of the (poly-)glycerol partial esters according to the present invention are that they make it possible to prepare stable cosmetic and dermatological O/W emulsions which can be preserved by using organic acids at pH values of 3.5 to 5.5. It is a further advantage that the (poly-)glycerol partial esters according to the present invention keep pigments or solids extremely stable in emulsion preparations.

DETAILED DESCRIPTION

The present invention, which provides (poly-)glycerol partial esters with one or more carboxylic acids having 10 to 24 carbon atoms and radicals of a polyfunctional carboxylic acid, comprising polyfunctional carboxylic acid ester (poly-) glycerol partial ester of the general formula (I) as described herein below, a process for their preparation, their use as emulsifiers and formulations which comprise the same, will now be described in greater detail.

Specifically, and in one embodiment, the present invention provides (poly-)glycerol partial esters with, on average (i.e., number-average), from 0.75 to 2.25 acid radicals of one or more carboxylic acids having 10 to 24, preferably 12 to 22, particularly preferably 14 to 18, carbon atoms and with, on average (number-average), from 0.005 to 0.5 radicals of a polyfunctional carboxylic acid, comprising polyfunctional carboxylic acid ester (poly-)glycerol partial ester, with the proviso that, following complete hydrolysis of the (poly-)

glycerol partial ester, a (poly-)glycerol is obtained which has a homologue distribution with (preferred ranges are given in brackets):
glycerol: 0.01% by weight to 20% by weight (3% by weight to 12% by weight),
diglycerols: 0.01% by weight to 60% by weight (20% by weight to 40% by weight),
triglycerols: 0.01% by weight to 60% by weight (15% by weight to 35% by weight),
tetraglycerols: 0.01% by weight to 30% by weight (5% by weight to 20% by weight),
pentaglycerols: 0.01% by weight to 20% by weight (0.1% by weight to 15% by weight) and
oligoglycerols: ad (i.e., in an amount sufficient to bring the mixture to) 100% by weight,
where the stated percentages by weight are based on the total amount of (poly-)glycerol and this distribution is determined using the GC method as explained below.

Within the context of the present invention, the term "polyfunctional carboxylic acid" is to be understood as meaning carboxylic acids which have more than one carboxyl group.

Polyfunctional carboxylic acids preferred according to the present invention are the dimer fatty acids specified in EP1683781, di- and tricarboxylic acids, in particular oxalic acid, fumaric acid, malonic acid, succinic acid, glutaric acid, adipic acid, pimelic acid, suberic acid, azelaic acid, sebacic acid, dodecanedioic acid, and also hydroxydi- and tricarboxylic acids, in particular malic acid, tartaric acid, tartronic acid, maleic acid and citric acid, and also aromatic acids, in particular phthalic acid, isophthalic acid or terephthalic acid, particular preference being given to citric acid.

Consequently, (poly-)glycerol partial esters particularly preferred according to the present invention are those (poly-)glycerol partial esters having on average (number-average) from 0.75 to 2.25 acid radicals of one or more carboxylic acids having 10 to 24, preferably 12 to 22, particularly preferably 14 to 18, carbon atoms and with on average (number-average) from 0.005 to 0.5 citric acid radicals, comprising citric acid ester (poly-)glycerol partial esters of the general formula (I):

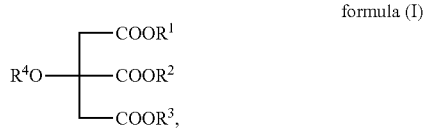

formula (I)

where $R^1$, $R^2$, $R^3$ and $R^4$, independently of one another, are identical or different and are selected from
H or
a radical of the general formula (II)

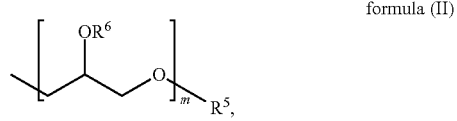

formula (II)

where m is greater than or equal to 1 and $R^5$ and $R^6$, independently of one another, are identical or different and are selected from
H or
an acyl radical having 10 to 24, preferably 12 to 22, particularly preferably 14 to 18, carbon atoms, where the acyl radical is determined by the acyl radical of the carboxylic acid esterified with the (poly-)glycerol and on average (number-average) at least one of the radicals $R^5$ or $R^6$=H, with the proviso that on average (number-average) at least one radical $R^1$, $R^2$ or $R^3$ is not H, and with the proviso that, following complete hydrolysis of the (poly-)glycerol partial ester, a (poly-)glycerol is obtained which has a homologue distribution with (preferred ranges are given in brackets):
glycerol: 0.01% by weight to 20% by weight (3% by weight to 12% by weight),
diglycerols: 0.01% by weight to 60% by weight (20% by weight to 40% by weight),
triglycerols: 0.01% by weight to 60% by weight (15% by weight to 35% by weight),
tetraglycerols: 0.01% by weight to 30% by weight (5% by weight to 20% by weight),
pentaglycerols: 0.01% by weight to 20% by weight (0.1% by weight to 15% by weight), and
oligoglycerols: ad 100% by weight,
where the stated percentages by weight are based on the total amount of (poly-)glycerol and this distribution is determined using the GC method as explained below.

One skilled in the art is aware that polyglycerol, on account of its polymeric property, constitutes a statistical mixture of different compounds. Polyglycerol can have formed ether bonds between two primary, one primary and one secondary, or two secondary, positions in the glycerol monomers; cyclic structures with one or more rings are likewise known. For details see, e.g., "Original synthesis of linear, branched and cyclic oligoglycerol standards", Cassel et al., Eur. J. Org. Chem. 2001, 875-896.

A suitable GC method for determining the homologue distribution includes the hydrolysis or alcoholysis of the (poly-)glycerol partial ester according to the present invention, separation of the polyglycerol from the resulting acids and analysis by gas chromatography.

For this, 0.6 g of the (poly-)glycerol partial ester according to the present invention are boiled in 25 ml of an ethanolic 0.5 M KOH solution under reflux for 30 minutes and the pH is adjusted to pH 2-3 with sulphuric acid. The resulting fatty acids are separated off by extraction three times with in each case one volume of petroleum ether. The combined extracts are concentrated by evaporation to approximately 10 ml.

A 0.5 ml sample is treated in an autosampler vessel with 0.5 ml of MTBE and 1 ml of trimethylanilinium hydroxide (0.2M in methanol) and analysed by GC. This is carried out in a gas chromatograph, which is equipped with a split/splitless injector, a capillary column and a flame ionization detector, under the following conditions:
Injector 290° C., split 30 ml
Injection volume: 1 µl
Column: 30 m *0.32 mm HP1 0.25 µm
Carrier gas: helium, head pressure 70 kPa
Temperature program: 80° C.-300° C. with 8° C./min, then conditioning for 20 minutes at 300° C.
Detector: FID at 320° C.
  hydrogen 35 ml/min
  air 240 ml/min
  make up gas 12 ml/min
Through this process, the fatty acids are separated as their methyl esters according to their carbon chain length. The relative content of the individual fatty acids can be determined by evaluating the peak areas.

The residue extracted with petroleum ether is adjusted to pH 7 to 8 with barium hydroxide, the precipitated barium sulphate is separated off by centrifugation. The supernatant is drawn off and the residue is extracted three times with 20 ml of ethanol.

The combined supernatants are concentrated by evaporation at 80° C. and 50 mbar, and the residue is taken up in pyridine. A 0.5 ml sample is treated in an autosampler vessel with 1 ml of N-methyl-N-trifluoroacetamide and heated at 80° C. for 30 minutes.

The polyglycerol is analysed as its trimethylsilyl derivative by means of GC, using a gas-liquid chromatograph with an on-column injector and flame ionization detector under the following conditions:
Injector: on-column, oven tray
Injection volume: 0.1 µl
Carrier gas: 3 ml/min hydrogen (constant flow)
Column: SimDist 12 m×0.32 mm×0.1 µm (Varian)
Temperature program: 65° C.-365° C., 10° C./min; then conditioning for 15 minutes at 365° C.
Detector (FID): 375° C.

Under these conditions, the polyglycerol is separated according to the degree of polymerization; additionally, cyclic isomers can be separated from linear isomers up to a polymerization degree of 5. The peak areas of the individual oligomers are separated from one another by a perpendicular at the lowest point between the peaks. Since the resolution for oligomers which have a higher degree of polymerization than 6 is low, the peak areas for heptaglycerol and higher oligomers are combined and taken into consideration for calculating the polydispersity index as heptaglycerol. Moreover, to calculate the polydispersity index, cyclic and linear isomers are combined. The relative content of the individual oligomers/isomers can be determined by evaluating the peak areas. In an analogous manner, this process can also be utilized in order to characterize the raw materials which are used for preparing the esters according to the present invention.

Suitable acyl radicals for $R^5$ and $R^6$ in the (poly-)glycerol partial esters according to the present invention are identical or different radicals, it being preferred that in this connection that the $R^5$ and $R^6$ radicals are different. The reason for this is the nature of the preparation process in which preferably technical-grade mixtures of carboxylic acids from which these acyl radicals arise are used. Preferred acyl radicals having 10 to 24, preferably 12 to 22, particularly preferably 14 to 18, carbon atoms are the acyl radicals of the acids lauric acid, tridecanoic acid, myristic acid, palmitic acid, margaric acid, stearic acid, isostearic acid, arachic acid and behenic acid, and also mixtures thereof. Naturally occurring mixtures are for example the coconut fatty acids which comprise, as main constituent, lauric acid, as well as saturated $C_{14}$-$C_{18}$-fatty acids, and optionally saturated $C_8$-$C_{10}$-fatty acids and unsaturated fatty acids, and also tallow fatty acids, which are essentially a mixture of palmitic acid and stearic acid and produce in this connection the particularly preferred acyl radicals, which can be varied widely within the ratio stearic acid to palmitic acid from 100:0.01 to 0.01:100. Preference is given to a weight ratio of 30:70 to 95:5, particularly a ratio of 45:55 to 90:10.

The acyl radicals of the monoolefinically unsaturated acids, for example hexadecenoic acids, octadecenoic acids, such as oleic acid (cis-9-octadecenoic acid) or elaidic acid (trans-9-octadecenoic acid), eicosenoic acids and docosenoic acids, such as erucic acid (cis-13-docosenoic acid) or brassidic acid (trans-13-docosenoic acid), and also the polyunsaturated fatty acids, for example octadecadienoic acids and octadecatrienoic acids, such as linoleic acid and linolenic acid, and mixtures thereof, are also suitable. In this connection, the liquid fatty acids such as oleic acid, ricinoleic acid, erucic acid and isostearic acid which contain 18 to 22 carbon atoms are particularly suitable. On account of a branching or of a double bond in the hydrocarbon chain, their solidification points are below 35° C. It is also possible to use fatty acid mixtures which can also comprise wax-like components, such as hydrogenated ricinoleic acid.

According to the present invention, it is preferable that the (poly-)glycerol obtained following complete hydrolysis of the (poly-)glycerol partial ester has an average degree of polymerization of from 2 to 6, preferably from 2.5 to 4.5 and very particularly preferably from 3 to 4.

For the calculation, the average degree of polymerization of the polyglycerol <n> is calculated via the hydroxyl value (OHV, in mg KOH/g) according to the formula <n>=(112200−18*OHV)/(74*OHV−56100).

Suitable determination methods for ascertaining the hydroxyl value are in particular those according to DGF C-V 17 a (53), Ph. Eur. 2.5.3 Method A and DIN 53240.

It is advantageous if the (poly-)glycerol obtained following complete hydrolysis of the (poly-)glycerol partial ester according to the present invention has a polydispersity index of 0.8 to 2.5, preferably from 1.0 to 1.8.

The polydispersity index can also be calculated as follows:

$$\sum_i |n_i - <n>| \cdot x_i,$$

where
$n_i$ is the degree of polymerization of the individual oligomer
<n> is the average degree of polymerization of the polyglycerol and
$x_i$ is the fraction of oligomer i in the polyglycerol, determined by the GC method described above.

Advantageous (poly-)glycerol partial esters according to the present invention are characterized in that, following complete hydrolysis of the (poly-)glycerol partial ester, the molar ratio of the resulting carboxylic acids derived from $R^5$ and $R^6$ to (poly-)glycerol is between 2:3 and 4:1, in particular between 1:1.2 and 3:1, very particularly preferably between 1:1 and 2:1.

To determine the molar ratios, the method which can be used is the GC method described above.

It is preferred according to the present invention that, following complete hydrolysis of the (poly-)glycerol partial ester, the molar ratio of the resulting polyfunctional carboxylic acid, in particular of the resulting citric acid, to (poly-)glycerol is between 1:2 and 1:200, in particular between 1:5 and 1:150, very particularly preferably between 1:10 and 1:100.

To determine the molar ratio, the method which can be used is the GC method described above.

(Poly-)glycerol partial esters preferred according to the present invention are characterized in that the ratio of saponification value (SV) to hydroxyl value (OHN) is between 1:1.3 and 1:2.6, in particular between 1:1.5 and 1:2.4, very particularly preferably between 1:1.6 and 1:2.2.

The acid value (AV) of the (poly-)glycerol partial esters according to the present invention is preferably <50, in particular <10, very particularly preferably <5.

Suitable determination methods for ascertaining the acid value are in particular those according to DGF C-V 2, Ph. Eur. 2.5.1, ISO 3682, ASTM D 974 and DIN EN ISO 2114, suitable determination methods for ascertaining the saponification value are DIN EN ISO 3657: 2003-12 and DIN 53401: 1988-06.

It is preferred according to the present invention that the (poly-)glycerol partial ester has a melting point greater than 35° C., preferably greater than 40° C., in particular greater than 45° C.

(Poly-)glycerol partial esters according to the present invention are obtainable by the process described below; consequently, the present invention further provides a process for the preparation of a (poly-)glycerol partial ester comprising polyfunctional carboxylic acid ester (poly-)glycerol partial ester involving the process steps A) provision of a (poly-)glycerol having a homologue distribution with (preferred ranges are given in brackets)
glycerol: 0.01 to 20 (3 to 12)% by weight
diglycerols: 0.01 to 60 (20 to 40)% by weight
triglycerols: 0.01 to 60 (15 to 35)% by weight
tetraglycerols: 0.01 to 30 (5 to 20)% by weight
pentaglycerols: 0.01 to 20 (0.1 to 10)% by weight
oligoglycerols: ad 100% by weight,
where the stated percentages by weight are based on the total amount of (poly-)glycerol and this distribution is determined using the GC method as explained above, B) esterification of some of the (poly-)glycerol with one or more carboxylic acids having 10 to 24, preferably 12 to 22, particularly preferably 14 to 18, carbon atoms and C) further esterification with a polyfunctional carboxylic acid, where the molar ratio of the polyfunctional carboxylic acid used in process step C) to (poly-)glycerol used in process step A) is 1:2 to 1:200, preferably 1:5 to 1:150, very particularly preferably 1:10 to 1:100.

Polyfunctional carboxylic acids used in the aforementioned process are preferably selected from the dimer fatty acids specified in EP1683781, oxalic acid, fumaric acid, malonic acid, succinic acid, glutaric acid, adipic acid, pimelic acid, suberic acid, azelaic acid, sebacic acid, dodecanedioic acid, malic acid, tartaric acid, tartronic acid, maleic acid, citric acid, phthalic acid, isophthalic acid and terephthalic acid, particular preference being given to using citric acid.

In an alternative embodiment of the process according to the present invention, process step C) can also be carried out before process step B).

The molar ratio, used in the process according to the present invention, of the carboxylic acids used in process step B) to (poly-)glycerol used in process step A) is preferably 2:3 to 4:1, in particular 1:1.2 to 3:1, very particularly preferably 1:1 to 2:1.

It is preferred according to the present invention that the average degree of polymerization of the polyglycerol used in step A) is 2 to 6, preferably 2.5 to 4.5 and very particularly preferably 3 to 4.

The (poly-)glycerol for process step A) can be provided by various methods such as, for example, polymerization of glycidol (e.g., base-catalysed), polymerization of epichlorohydrin (for example in the presence of equimolar amounts of a base such as NaOH) or polycondensation of glycerol. According to the present invention, preference is given to the provision of the (poly-)glycerol via the condensation of glycerol, in particular in the presence of catalytic amounts of a base, in particular NaOH or KOH. Suitable reaction conditions are temperatures between 220-260° C. and reduced pressure in a range between 20 to 800 mbar, in particular between 50 and 500 mbar, which makes it easier to remove the water.

A particularly preferred process for the provision of the (poly-)glycerol with the required homologue distribution, which, in addition to this, leads to a high polydispersity index and the preferred degree of polymerization, involves the process steps A1) reaction of glycerol in the presence of a catalytic amount of base, preferably 0.2 to 5% by weight of NaOH or KOH, based on the total reaction mixture, in a temperature range of 220-260° C. and in a pressure range between 250 and 1000 mbar, preferably with distillative separation of water, until the reaction mixture comprises less than 70% by weight, preferably less than 60% by weight, of glycerol, based on the total reaction mixture, A2) further reaction at reduced pressure in a range from 20 to 200 mbar with distillative separation of water and glycerol, until the hydroxyl value of the reaction mixture is less than 1400, preferably less than 1200, and, optionally, A3) neutralization of the catalyst with an acid, preferably a mineral acid.

In the process according to the present invention, process steps B) and C) are carried out under conditions for esterification reactions that are well known to a person skilled in the art, if appropriate in the presence of a catalyst. In particular, this esterification is carried out with removal of water from the reaction mixture.

Process step B) is preferably carried out at 180-260° C., particularly preferably 210-250° C., process step C) preferably at 100-170° C., particularly preferably at 120-140° C.

The course of the reaction can be monitored, for example, via the acid value of the product, meaning that in process steps B) and C) it is preferred to continue until the desired acid value is reached. In step C) the polyfunctional carboxylic acid used is generally not completely esterified, but reacted such that the (poly-)glycerol partial esters according to the present invention in part still contain free carboxyl groups.

The carboxylic acids used in process step B) are preferably those which have been specified above as preferred carboxylic acids supplying the acyl radicals $R^5$ and $R^6$ in the (poly-)glycerol partial esters according to the present invention. In particular, in this connection, the aforementioned tallow fatty acids with the described ratios of palmitic acid and stearic acid are used.

(Poly-)glycerol partial esters according to the present invention and (poly-)glycerol partial esters obtainable or obtained by the process according to the present invention are exceptionally suitable for use as a high-performance O/W emulsifier which is based exclusively on renewable raw materials and has a high formulation flexibility, especially in cosmetic formulations.

Consequently, emulsions comprising (poly-)glycerol partial esters according to the present invention or (poly-)glycerol partial esters obtainable or obtained by the process according to the present invention are also provided herein. Within the context of this invention, an emulsifier is to be understood as meaning an emulsifier which consists of at least one (poly-)glycerol partial ester according to the present invention or (poly-)glycerol partial ester obtainable or obtained by the process according to the present invention and, if appropriate, at least one coemulsifier, the presence of a coemulsifier being preferred.

(Poly-)glycerol partial esters according to the present invention and (poly-)glycerol partial esters obtainable or obtained by the process according to the present invention are also suitable for use for producing cosmetic or pharmaceutical formulations, in particular for producing cosmetic creams and lotions.

In this connection, creams and lotions are understood as meaning cosmetic O/W emulsions with spreadable-pasty or flowable consistency.

In general, the (poly-)glycerol partial esters according to the present invention can be used, for example, in care creams and lotions for face, body and hands, in sunscreen emulsions, in make-up, in aerosols, roll-ons, pump sprays, sticks e.g., in the antiperspirant/deodorant sector, in baby care products, in intimate care products, foot care products, hair care products, nail care products, dental care products or oral care products, and also in dermatological salves.

Consequently, cosmetic or pharmaceutical formulations, in particular O/W formulations, comprising (poly-)glycerol partial esters according to the present invention or (poly-)glycerol partial esters obtainable or obtained by the process according to the present invention are also provided herein. Formulations preferred according to the present invention are sunscreen preparations and O/W make-up formulations.

Formulations preferred according to the present invention comprise the (poly-)glycerol partial ester according to the present invention or (poly-)glycerol partial ester obtainable or obtained by the process according to the present invention in amounts of from 0.01 to 10% by weight, preferably 0.05 to 8% by weight and particularly preferably 0.1 to 5% by weight, based on the total formulation.

The formulations according to the present invention can comprise e.g., at least one additional component selected from the group of
emollients,
coemulsifiers,
thickeners/viscosity regulators/stabilizers,
antioxidants,
hydrotropes (or polyols),
solids and fillers,
pearlescence additives,
deodorant and antiperspirant active ingredients,
insect repellents,
self-tanning agents,
preservatives,
conditioners,
perfumes,
dyes,
cosmetic active ingredients,
care additives,
superfatting agents, and
solvents.

Substances which can be used as exemplary representatives of the individual groups are known to a person skilled in the art and can be found for example in German Application DE 102008001788.4. This patent application is hereby incorporated by reference and thus forms part of the disclosure.

In regard to optional components and their amounts of the optional components used, reference is made expressly to the relevant handbooks known to the person skilled in the art, e.g., K. Schrader, "Grundlagen and Rezepturen der Kosmetika [Fundamentals and Formulations of Cosmetics]", 2nd edition, page 329 to 341, Hüthig Buch Verlag Heidelberg.

The amounts of the additives in question are governed by the intended use.

Typical guideline formulations for the particular applications are known prior art and are contained for example in the brochures of the manufacturers of the respective raw materials and active ingredients. These existing formulations can generally be transferred without modification. If necessary, however, the desired modifications can be undertaken without complication by means of simple experiments for the purposes of adaptation and optimization.

Since the (poly-)glycerol partial esters and emulsifiers according to the present invention can keep pigments or solids extremely stable in emulsion preparations, solids and fillers, in particular particles and additives, which are used for achieving a specific skin feel, such as e.g., silicone elastomers, PMMA particles, PE particles, PS particles, nylon particles, boron nitride, starch, mica and talc, are a preferred additional component.

According to the present invention, preference is given to formulations which comprise, as preservatives, organic acids, in particular sorbic acid, benzoic acid and/or dehydroacetic acid, especially in a range from 0.01 to 1.0% by weight, based on the total formulation.

Furthermore, formulations preferred according to the present invention have a pH of from 3.5 to 5.5, in particular from 4.0 to 5.0.

It has been found that the (poly-)glycerol partial esters according to the present invention are exceptionally suitable for increasing the water resistance of formulations according to the present invention. This is advantageous especially for sunscreen preparations and also for O/W make-up formulations. Consequently, the present invention further provides the use of the (poly-)glycerol partial esters according to the present invention or (poly-)glycerol partial esters obtainable or obtained by the process according to the present invention, and also the emulsifiers according to the present invention for improving the water resistance of cosmetic or pharmaceutical formulations, especially of sunscreen preparations, these preferably comprising pigments or solid bodies, in particular titanium oxide.

In this connection, water resistance is understood as meaning preventing the formulation from readily being removed from a surface, in particular from skin, as a result of contact with water. The water resistance can be determined by a simple in-vitro test described as in Int. J. Cosm. Sci., 2007, 29, 451-460.

In the examples listed below, the present invention is described by way of example without any intention to limit the present invention, the scope of which arises from the entire description and the claims, to the embodiments specified in the examples.

Unless stated otherwise, all of the percentages (%) given are percentages by mass.

EXAMPLES

Example 1

Emulsifier 1

90 g of polyglycerol, with an average OH number of 1190 mg KOH/g, was reacted with 210 g of stearic acid at 240° C. with the introduction of nitrogen. The water of reaction was distilled off. At an acid value of <2 mg KOH/g, the polyglycerol ester was cooled to 130° C., 40 g of citric acid was added, and the pressure was reduced to 50 mbar. The water, which was formed in this reaction, was separated off again. At an acid value <50, the vacuum was broken with nitrogen and the product was drawn off.
OH number: 237 mg KOH/g
AV: 45 mg KOH/g
Saponification value: 189 mg KOH/g Example 2

Emulsifier 2

137.2 g of polyglycerol, with an average OH number of 1120 mg KOH/g, was reacted with 254.8 g of stearic acid at 240° C. with the introduction of nitrogen. The water of reaction was distilled off. At an acid value of <2 mg KOH/g, the polyglycerol ester was cooled to 130° C., 8 g of citric acid was added, and the pressure was reduced to 50 mbar. The water, which was formed during the reaction, was separated off again. At an acid value of <1, the vacuum was broken with nitrogen and the product was drawn off.
OH number: 235 mg KOH/g
AV: 2.3 mg KOH/g
Saponification value: 145 mg KOH/g Example 3

Emulsifier 3

152.8 g of polyglycerol, with an average OH number of 1000 mg KOH/g, was reacted with 229.2 g of stearic acid at 240° C. with the introduction of nitrogen. The water of reaction was distilled off. At an acid value of <2 mg KOH/g, the polyglycerol ester was cooled to 130° C., 18 g of citric acid was added, and the pressure was reduced to 50 mbar. The water, which was formed during the reaction, was separated off again. At an acid value of <3 mg KOH/g, the vacuum was broken with nitrogen and the product was drawn off.
OH number: 241 mg KOH/g
AV: 2.6 mg KOH/g
Saponification value: 140 mg KOH/g Example 4

Emulsifier 4

114.6 g of polyglycerol, with an average OH number of 1120 mg KOH/g, was reacted with 267.4 g of palmitic acid at 240° C. with the introduction of nitrogen. The water of reaction was distilled off. At an acid value of <2 mg KOH/g, the polyglycerol ester was cooled to 130° C., 18 g of citric acid was added and the pressure was reduced to 50 mbar. The water, which was formed during the reaction, was separated off again. At an acid value of <3 mg KOH/g, the vacuum was broken with nitrogen and the product was drawn off.
OH number: 189 mg KOH/g
AV: 2.8 mg KOH/g
Saponification value: 148 mg KOH/g Example 5

Emulsifier 5

133.7 g of polyglycerol, with an average OH number of 1000 mg KOH/g, was reacted with 248.3 g of behenic acid at 240° C. with the introduction of nitrogen. The water of reaction was distilled off. At an acid value of <2 mg KOH/g, the polyglycerol ester was cooled to 130° C., 18 g of citric acid was added, and the pressure was reduced to 50 mbar. The water, which was formed during the reaction, was separated off again. At an acid value of <3 mg KOH/g, the vacuum was broken with nitrogen and the product was drawn off.
OH number: 287.9 mg KOH/g
AV: 2.8 mg KOH/g
Saponification value: 111 mg KOH/g Application Examples All of the concentrations in the application examples are given in per cent by weight. To prepare the emulsions, customary homogenization methods known to the person skilled in the art were used.

The emulsions were therefore typically prepared in such a way that the oil phase and the water phase were heated to 70-75° C. Then, either the oil phase was stirred into the water, or the oil phase and water phase were combined without stirring.

Homogenization was then carried out using a suitable homogenizer (e.g., Ultrathurrax) for approximately 1-2 minutes.

Stabilizing polymers (e.g., carbomers) were preferably stirred into the emulsion as oil dispersion at temperatures of 50-60° C. The mixture was then briefly homogenized. Further ingredients (e.g., preservatives, active ingredients) were preferably added at 40° C. If the formulations were preserved with organic acids, the pH of the emulsions was adjusted to approximately 5.

Differentiation of the Performance Against the Prior Art

These experiments are intended to show that the polyglycerol partial esters according to the present invention have advantages with regard to emulsion stability. The representatives of O/W emulsifiers based completely on natural raw materials chosen here were glyceryl stearate citrate, polyglyceryl-3 distearate and a customary combination of sorbitan stearate and sucrose cocoate, e.g., C1, C2, and C3, respectively.

To examine the storage stability of the emulsions, they were stored for three months at room temperature, 40° C. and 45° C. To examine the low-temperature stability, the emulsions were moreover stored for one month at −5° C., and three freeze-thaw cycles of 25° C./−15° C./25° C. were carried out. Significant changes in appearance or consistency and in particular oil or water depositions were weighted as criteria for instability. In order to ensure a fair comparison, the amount of emulsifier and the corresponding amount of consistency regulator (stearyl alcohol, glyceryl stearate) were in each case optimized to the corresponding type of emulsifier. The total oil phase content was always adjusted to 25.0%.

Consequently, it could be ensured that the examples according to the present invention had a starting consistency comparable with the emulsions containing the comparison emulsifiers.

Comparison in Cream Formulation:

|  | Examples | | | |
|---|---|---|---|---|
|  | 1 | C1 | C2 | C3 |
| Emulsifier 2 | 3.0% | | | |
| Glyceryl stearate citrate[1] | | 1.50% | | |
| Polyglyceryl-3 distearate[2] | | | 3.0% | |
| Sorbitan stearate; Sucrose cocoate[3] | | | | 4.0% |
| Stearyl alcohol | 1.0% | 6.0% | 1.0% | 2.5% |

-continued

|  | Examples | | | |
| --- | --- | --- | --- | --- |
|  | 1 | C1 | C2 | C3 |
| Glyceryl stearate | 2.0% |  | 2.0% | 2.5% |
| Isopropyl palmitate | 5.0% | 5.0% | 5.0% | 4.5% |
| Caprylic/capric triglyceride | 9.0% | 7.5% | 9.0% | 7.0% |
| Avocado oil | 5.0% | 5.0% | 5.0% | 4.5% |
| Glycerol | 3.0% | 3.0% | 3.0% | 3.0% |
| Demineralized water | ad 100% | ad 100% | ad 100% | ad 100% |
| Benzyl alcohol, benzoic acid, sorbic acid[4] | 1.0% | 1.0% | 1.0% | 1.0% |
| NaOH (5% solution) (pH adjustment to 5.0) | q.s. (a sufficient quantity) | q.s. | q.s. | q.s. |
| Consistency after preparation | pasty, cream-like | pasty, cream-like | pasty, cream-like | pasty, cream-like |
| Stability | stable | water separation after 2 months at 45° C.; pH drop to 4.5 | water separation after 1 week at 40° C. and 45° C. | water separation after 1 month at RT and 40° C. and after 1 week at 45° C. |

[1] AXOL ® C 62 (Evonik Goldschmidt)
[2] Cremophor ® GS 32 (BASF)
[3] Arlatone ® 2121 (Croda)
[4] Rokonsal ® BSB-N (ISP)

Whereas the formulation with emulsifier 2 according to the present invention leads to a storage-stable formulation, the creams containing the comparison emulsifiers exhibit considerable weaknesses in the storage stability.

A further comparison of a (poly-)glycerol partial ester according to the present invention against polyglyceryl-3 distearate (C4) and the combination of sorbitan stearate and sucrose stearate (C5) was carried out in a O/W lotion.

|  | Examples | | |
| --- | --- | --- | --- |
|  | 2 | C4 | C5 |
| Emulsifier 2 | 3.0% |  |  |
| Polyglyceryl-3 distearate[2] |  | 3.0% |  |
| Sorbitan stearate; sucrose cocoate[3] |  |  | 3.0% |
| Isopropyl palmitate | 2.5% | 2.5% | 2.5% |
| Caprylic/capric triglyceride | 4.5% | 4.5% | 4.5% |
| Avocado oil | 5.0% | 5.0% | 5.0% |
| Glycerol | 3.0% | 3.0% | 3.0% |
| Xanthan gum | 0.5% | 0.5% | 0.5% |
| Demineralized water | ad 100% | ad 100% | ad 100% |
| Benzyl alcohol, benzoic acid, sorbic acid[4] | 1.0% | 1.0% | 1.0% |
| NaOH (5% solution) (pH adjustment to 5.0) | q.s. | q.s. | q.s. |
| Consistency after preparation | flowable | flowable | flowable |
| Stability | stable | severe water separation after 1 month at 45° C. | emulsion separates completely after 1 month at 45° C. |

Here, it is also shown that the use of the (poly-)glycerol partial ester according to the present invention leads to a considerably improved elevated-temperature stability compared to the comparison emulsifiers.

Further Emulsion Examples

These examples are intended to show that the (poly-)glycerol partial esters according to the present invention can be used in a large number of cosmetic formulations.

Moreover, with the help of the (poly-)glycerol partial esters according to the present invention, it is possible to stably incorporate pigments or solids into emulsion preparations.

Furthermore, the examples exhibit good compatibility with typical coemulsifiers, oils, thickeners and stabilizers.

| O/W Lotions | | | | | |
| --- | --- | --- | --- | --- | --- |
|  | Examples | | | | |
|  | 3 | 4 | 5 | 6 | 7 |
| Emulsifier 2 | 3.0% |  | 3.0% |  |  |
| Emulsifier 3 |  | 2.0% |  |  | 3.0% |
| Emulsifier 4 |  |  |  | 3.0% |  |
| Isopropyl palmitate | 2.5% | 3.0% |  |  |  |
| Caprylic/capric triglyceride | 4.5% | 7.0% | 5.0% |  |  |
| Almond oil | 5.0% |  |  |  |  |
| Avocado oil |  |  | 5.0% |  |  |
| Diethylhexyl carbonate |  |  |  |  | 7.0% |
| Ethylhexyl palmitate |  | 7.3% | 6.5% | 5.8% | 5.8% |
| Mineral oil |  | 6.5% |  |  |  |
| PPG-15 stearyl ether |  |  |  | 2.0% |  |
| Ceramide 3 |  |  | 0.2% |  |  |
| Salicyloyl phytosphingosine |  |  |  | 0.2% |  |
| Cetyl ricinoleate |  |  | 2.0% |  |  |
| Dimethicone/vinyl dimethicone crosspolymer |  |  |  | 2.0% |  |
| Glycerol | 5.0% | 3.0% | 3.0% | 3.0% | 3.0% |
| Hydrolysed hyaluronic acid |  |  |  |  | 0.2% |
| Xanthan gum | 0.5% |  | 0.5% |  |  |
| Carbomer |  | 0.2% |  | 0.2% | 0.2% |

-continued

| | | | | | |
|---|---|---|---|---|---|
| Demineralized water | ad 100% | ad 100% | ad 100% | ad 100% | ad 100% |
| Benzyl alcohol, benzoic acid, sorbic acid[4] | 1.0% | | 1.0% | | |
| NaOH (5% solution) (pH adjustment to 5.0) | | q.s. | | q.s. | |
| Phenoxyethanol, ethylhexylglycerol[5] | | 0.8% | | | |
| Methylisothiazolinone, methylparaben, ethylparaben; dipropylene glycol[6] | | | | 0.8% | 0.8% |

O/W Creams

| | Examples | | | | |
|---|---|---|---|---|---|
| | 8 | 9 | 10 | 11 | 12 |
| Emulsifier 2 | 3.0% | | 2.0% | | 2.0% |
| Emulsifier 3 | | 3.0% | | 2.8% | |
| Glyceryl stearate | 2.0% | 2.0% | 2.0% | 2.0% | 3.5% |
| Stearyl alcohol | 1.0% | 2.0% | 1.0% | 2.0% | 1.5% |
| Distearyldimonium chloride | | | 1.0% | | |
| Sodium cetearyl sulphate | | | | 0.2% | |
| Bis-PEG/PPG-20/5 PEG/PPG-20/5 dimethicone, methoxy PEG/PPG-25/4 dimethicone; caprylic/capric triglyceride[8] | | | | 1.0% | |
| Isopropyl palmitate | 10.3% | | | 10.0% | |
| Caprylic/capric triglyceride | | 7.5% | 10.0% | 5.0% | |
| Almond oil | | | 5.0% | | |
| Avocado oil | | 5.0% | | | |
| Diethylhexyl Carbonate | 9.5% | | | | 8.5% |
| Ethylhexyl palmitate | | | 9.0% | | 5.0% |
| Decyl cocoate | | 7.0% | | | |
| Dimethicone | | | | | 2.0% |
| Cetyl ricinoleate | | | | | 1.0% |
| Glycerol | 3.0% | 3.0% | 6.0% | 3.0% | |
| Tetrapeptide-17, glycerol, butylene glycol, aqua[7] | 2.5% | | | | |
| Curcuma Longa (turmeric root extract) | | 0.5% | | | |
| Carbomer | 0.2% | | | | |
| Demineralized water | ad 100% | ad 100% | ad 100% | ad 100% | ad 100% |
| Benzyl alcohol, benzoic acid, sorbic acid[4] | | 1.0% | | 1.0% | |
| NaOH (5% solution) (pH adjustment to 5.0) | | q.s. | | q.s. | |
| Methylisothiazolinone, methylparaben, ethylparaben; dipropylene glycol[6] | 0.8% | | | 0.8% | |
| Phenoxyethanol, ethylhexylglycerol[5] | | | 0.7% | | |

[5] Euxyl ® PE 9010 (Schülke)
[6] Microcare ® MEM (Thor)
[7] TEGO ® Pep 4-17 (Evonik Goldschmidt)
[8] ABIL ® Care XL 80 (Evonik Goldschmidt)

Sunscreen Lotion:

| | Example 13 |
|---|---|
| Emulsifier 2 | 3.0% |
| Glyceryl stearate | 0.5% |
| Stearyl alcohol | 0.5% |
| Diethylhexyl carbonate | 3.0% |
| Caprylic/capric triglyceride | 2.0% |
| C12-15 alkyl benzoate | 5.0% |
| Octocrylene | 2.0% |
| Bis-Ethylhexyloxyphenol methoxyphenyl triazine | 3.0% |
| Polysilicone-15 | 2.0% |
| Titanium dioxide; trimethoxycaprylylsilane | 5.0% |
| Glycerol | 3.0% |
| Xanthan gum | 0.2% |
| Carbomer | 0.3% |
| Demineralized water | ad 100% |
| NaOH (5% solution) (pH adjustment to 6.0) | q.s. |
| Methylisothiazolinone, methylparaben, ethylparaben; dipropylene glycol[6] | 0.8% |

Self-Tanning Lotion:

| | Example 13 |
|---|---|
| Emulsifier 3 | 3.0% |
| Ceteareth-25 | 0.5% |
| Glyceryl stearate | 2.5% |
| Stearyl alcohol | 1.0% |
| Isopropyl palmitate | 3.0% |
| Caprylic/capric triglyceride | 3.0% |
| Mineral oil | 7.0% |
| Jojoba oil | 3.0% |
| Glycerol | 3.0% |
| Dihydroxyacetone | 5.0% |
| Demineralized water | ad 100% |
| Citric Acid (10% solution) (pH adjustment to 4.0) | q.s. |
| Methylisothiazolinone, methylparaben, ethylparaben; dipropylene glycol[6] | 0.8% |

Hair Cream with UV Protection:

| | Example 13 |
|---|---|
| Emulsifier 5 | 3.0% |
| Caprylic/capric triglyceride | 4.0% |
| Apricot kernel oil | 2.5% |
| Almond oil | 2.5% |
| Cetearyl ricinoleate | 1.0% |
| Isopropyl myristate | 2.0% |
| Cetearyl alcohol | 1.0% |
| Glyceryl stearate | 1.5% |
| Glycerol | 3.0% |
| Ethylhexyl methoxycinnamate | 2.0% |
| Polysilicone-19 | 0.5% |
| Silicone quaternium-22 | 0.2% |
| Demineralized water | ad 100% |
| Methylisothiazolinone, methylparaben, ethylparaben; dipropylene glycol[6] | 0.8% |

PEG-Free AP/Deo Roll-On:

|  | Example 14 |
|---|---|
| Emulsifier 2 | 2.5% |
| Caprylic/capric triglyceride | 2.0% |
| Diethylhexyl Carbonate | 2.5% |
| PPG-14 Butylether | 2.5% |
| Polyglyceryl-3 Caprylate | 1.0% |
| Palmitamidopropyltrimonium Chloride | 1.0% |
| Demineralized water | ad 100% |
| Hydroxyethyl Cellulose | 1.0% |
| Silicone quaternium-22 | 0.2% |
| Parfum | q.s. |
| Methylisothiazolinone, methylparaben, ethylparaben; dipropylene glycol[6] | 0.8% |

While the present disclosure has been particularly shown and described with respect to various embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

The invention claimed is:

1. A (poly-)glycerol partial ester having, on average, from 0.75 to 2.25 acid radicals of one or more carboxylic acids having 10 to 24 carbon atoms and having, on average, from 0.005 to 0.5 radicals of a polyfunctional carboxylic acid comprising polyfunctional carboxylic acid ester (poly-)glycerol partial ester with the proviso that, following complete hydrolysis of the (poly-)glycerol partial ester, a (poly-)glycerol is obtained which has a homologue distribution with:
glycerol: 0.01% by weight to 20% by weight,
diglycerols: 0.01% by weight to 60% by weight,
triglycerols: 0.01% by weight to 60% by weight,
tetraglycerols: 0.01% by weight to 30% by weight,
pentaglycerols: 0.01% by weight to 20% by weight, and
oligoglycerols: ad 100% by weight.

2. The (poly-)glycerol partial ester according to claim 1, wherein the polyfunctional carboxylic acid is citric acid and comprises citric acid ester (poly-)glycerol partial ester of the general formula (I):

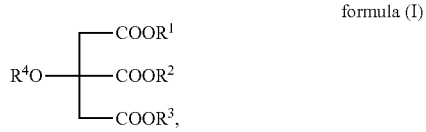

formula (I)

where $R^1$, $R^2$, $R^3$ and $R^4$, independently of one another, are identical or different and are selected from
H or
a radical of the general formula (II)

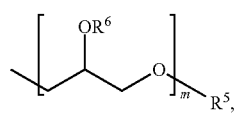

formula (II)

where m is greater than or equal to 1 and $R^5$ and $R^6$, independently of one another, are identical or different and are selected from
H or
an acyl radical having 10 to 24 carbon atoms,
where the acyl radical is determined by the acyl radical of the carboxylic acid
esterified with the (poly-)glycerol
and on average at least one of the radicals $R^5$ or $R^6$ =H,
with the proviso that on average at least one radical $R^1$, $R^2$ or $R^3$ is not H.

3. The (poly-)glycerol partial ester according to claim 2, wherein following complete hydrolysis of the partial ester, the molar ratio of the resulting carboxylic acids derived from $R^5$ and $R^6$ to (poly-)glycerol is between 2:3 and 4:1.

4. The (poly-)glycerol partial ester according to claim 1, wherein said (poly-)glycerol partial ester has a ratio of saponification value to hydroxyl value between 1:1.3 and 1:2.6.

5. The (poly-)glycerol partial ester according claim 1, wherein the acid value is less than 50.

6. The (poly-)glycerol partial ester according to claim 1, wherein the (poly-)glycerol partial ester has a melting point greater than 35° C.

7. The (poly-)glycerol partial ester according to claim 2, wherein the acyl radical determining $R^5$ and $R^6$ arises from a mixture of stearic acid and palmitic acid in a weight ratio from 30:70 to 95:5.

8. A process for the preparation of a (poly-)glycerol partial ester comprising:
providing a (poly-)glycerol having a homologue distribution with
glycerol: 0.01 to 20% by weight
diglycerols: 0.01 to 60% by weight
triglycerols: 0.01 to 60% by weight
tetraglycerols: 0.01 to 30% by weight
pentaglycerols: 0.01 to 20% by weight, and
oligoglycerols: ad 100% by weight;
first esterifying some of the (poly-)glycerol with one or more carboxylic acid having 10 to 24 carbon atoms; and
second esterifying with a polyfunctional carboxylic acid, where the molar ratio of the polyfunctional carboxylic acid used in the second esterifying step to (poly-)glycerol used in said providing step is 1:2 to 1:200, to provide a (poly-)glycerol partial ester having, on average, from 0.75 to 2.25 acid radicals of said one or more carboxylic acids having 10 to 24 carbon atoms and having, on average, from 0.005 to 0.5 radicals of said polyfunctional carboxylic acid.

9. The process according to claim 8, wherein the one or more carboxylic acids to (poly-)glycerol used have a molar ratio of 2:3 to 4:1.

10. The process according to claim 8, wherein the polyfunctional carboxylic acid is citric acid and the carboxylic acid is a mixture of stearic acid and palmitic acid in a weight ratio from 30:70 to 95:5.

11. An emulsifier comprising the (poly-)glycerol partial ester according to claim 1.

12. A formulation comprising the (poly-)glycerol partial ester according to claim 1.

13. The formulation according to claim 12, wherein the (poly-)glycerol partial ester is present in an amount from 0.01 to 10% by weight.

14. The formulation according to claim 12, further comprising from 0.01 to 1.0% by weight of at least one organic acid preservative.

15. The formulation according to claim 12, wherein said formulation has a pH of from 3.5 to 5.5.

\* \* \* \* \*